United States Patent
Mogensen et al.

(10) Patent No.: US 10,369,277 B2
(45) Date of Patent: Aug. 6, 2019

(54) INVISIBLE NEEDLE

(75) Inventors: Lasse W. Mogensen, Søborg (DK);
Orla Mathiasen, Sorø (DK)

(73) Assignee: UNOMEDICAL A/S (DK)

( * ) Notice: Subject to any disclaimer, the term of this patent is extended or adjusted under 35 U.S.C. 154(b) by 753 days.

(21) Appl. No.: 11/519,137

(22) Filed: Sep. 11, 2006

(65) Prior Publication Data

US 2007/0093754 A1    Apr. 26, 2007

Related U.S. Application Data

(60) Provisional application No. 60/716,222, filed on Sep. 12, 2005.

(30) Foreign Application Priority Data

Sep. 12, 2015    (EP) .................................... 05019774

(51) Int. Cl.
*A61M 5/158* (2006.01)
*A61M 5/32* (2006.01)
*A61M 39/02* (2006.01)

(52) U.S. Cl.
CPC ............. *A61M 5/158* (2013.01); *A61M 5/326* (2013.01); *A61M 39/02* (2013.01);
(Continued)

(58) Field of Classification Search
CPC ...... A61M 2005/1585; A61M 25/0606; A61M 2005/14252; A61M 25/06–0631;
(Continued)

(56) References Cited

U.S. PATENT DOCUMENTS 643,544 A    2/1900  Simmons
1,592,462 A  7/1926  MacGregor
(Continued)

FOREIGN PATENT DOCUMENTS

DE    893 296      12/1953
DE    1 053 541    3/1959
(Continued)

OTHER PUBLICATIONS

"Why Inset®?" Inset® infusion set product overview; http://web.archive.org/web/20040906102448/http://www.infusion-set.com/Default.asp?ID=108; two pages.

*Primary Examiner* — Bhisma Mehta
*Assistant Examiner* — Laura C Schell
(74) *Attorney, Agent, or Firm* — Wilson Sonsini Goodrich & Rosati

(57) ABSTRACT

The invention relates to an inserter for an infusion set for intermittent or continuous administration of a therapeutical substance, such as e.g. insulin. The inserter comprises a needle hub comprising an insertion needle and two spring units assuring automatic insertion and automatic retraction of the insertion needle.

The inserter comprises a housing (1), a carrier body (2) carrying an infusion part (8), a needle hub (3), a first moving unit (4) bringing the carrier body (2) to a forward position and a second moving unit (5) bringing the carrier body (2) to a retracted position. The inserter is characterized in that it has means for activation which should be activated at least once in order to bring the carrier body (2) from a retracted to a forward position, and back from the forward to the retracted position.

25 Claims, 5 Drawing Sheets

(52) U.S. Cl.
CPC .............. *A61M 2005/1581* (2013.01); *A61M 2005/1585* (2013.01); *A61M 2005/1587* (2013.01)

(58) Field of Classification Search
CPC ...... A61M 25/065; A61M 2005/14256; A61M 2005/1583; A61M 5/158; A61M 2005/1586; A61M 2005/1587; A61B 17/3417; A61B 17/3496; A61B 17/3474; A61B 17/34; A61B 2017/3403; A61B 2017/3405; A61B 2017/3407; A61B 2017/3409; A61B 17/3415
USPC ...... 604/156, 157, 264, 523, 167.01–167.04, 604/164.01, 164.04, 288.01, 288.02, 136, 604/117, 134, 272, 164.07, 164.12, 604/165.01, 180
See application file for complete search history.

(56) References Cited

U.S. PATENT DOCUMENTS

| | | |
|---|---|---|
| 1,838,825 A | 1/1929 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoom |
| 2,972,779 A | 2/1961 | Cowley |
| 3,055,361 A | 9/1962 | Ballard |
| 3,059,802 A | 10/1962 | Mitchell |
| 3,107,785 A | 10/1963 | Roehr |
| 3,074,541 A | 11/1963 | Roehr |
| 3,149,186 A | 9/1964 | Coanda |
| 3,154,080 A | 10/1964 | Rowan et al. |
| 3,221,739 A | 12/1965 | Rosenthal |
| 3,221,740 A | 12/1965 | Rosenthal |
| 3,306,291 A | 2/1967 | Burke |
| 3,317,166 A | 5/1967 | Janssen |
| 3,485,352 A | 12/1969 | Pilger |
| 3,509,879 A | 5/1970 | Bathish et al. |
| 3,519,158 A | 7/1970 | Anderson |
| 3,545,286 A | 8/1970 | Stenstrom |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,648,999 A | 3/1972 | Bauer |
| 3,670,727 A | 6/1972 | Reiterman |
| 3,783,895 A | 1/1974 | Weichselbaum |
| 3,783,996 A | 1/1974 | Gerard et al. |
| 3,788,374 A | 1/1974 | Saijo |
| 3,810,469 A | 5/1974 | Hurschman |
| 3,831,729 A | 5/1974 | Howard |
| 3,814,097 A | 6/1974 | Ganderton et al. |
| 3,835,862 A | 9/1974 | Villari |
| 3,840,011 A | 10/1974 | Wright |
| 3,865,236 A | 2/1975 | Rycroft |
| 3,893,448 A | 7/1975 | Brantigan |
| 3,937,219 A | 2/1976 | Karakashian |
| 3,942,528 A | 3/1976 | Loeser |
| 3,986,507 A | 10/1976 | Watt |
| 3,986,508 A | 10/1976 | Barrington |
| 3,995,518 A | 12/1976 | Spiroff |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,306,705 A | 12/1981 | Svenson |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,365,630 A | 12/1982 | McFlarlane |
| 4,378,015 A | 3/1983 | Wardlaw |
| 4,400,861 A | 8/1983 | Parker |
| 4,402,407 A | 9/1983 | Maly |
| 4,406,042 A | 9/1983 | McPhee |
| 4,415,393 A | 11/1983 | Grimes |
| 4,417,886 A | 11/1983 | Frankhouser et al. |
| 4,458,344 A | 7/1984 | Coogler |
| 4,472,024 A | 7/1984 | Konomura et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,517,971 A | 5/1985 | Sorbonned |
| 4,525,157 A | 6/1985 | Vaillancourt |
| 4,530,695 A | 7/1985 | Phillips et al. |
| 4,531,686 A | 7/1985 | Shaw |
| 4,531,937 A | 7/1985 | Yates |
| 4,543,088 A | 9/1985 | Bootman et al. |
| 4,563,177 A | 1/1986 | Kamen |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,617,019 A | 10/1986 | Fecht |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,727,999 A | 3/1988 | Gach |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A * | 1/1990 | Miskinyar ......... A61M 5/14248 604/136 |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,030,206 A * | 7/1991 | Lander ............... A61B 17/3496 604/164.12 |
| 5,067,496 A | 11/1991 | Eisele |

(56) References Cited

U.S. PATENT DOCUMENTS

| | | |
|---|---|---|
| 5,077,872 A | 1/1992 | Guthammar |
| 5,083,757 A | 1/1992 | Barsky |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,129,884 A | 7/1992 | Dysarz |
| 5,134,593 A | 7/1992 | Logan et al. |
| 5,134,594 A | 7/1992 | Woo |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,152,754 A * | 10/1992 | Plyley et al. ............ 604/164.12 |
| 5,161,681 A | 11/1992 | Kemp et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,314 A | 2/1993 | Peters |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,433,307 A | 7/1995 | Jeppe |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,487,506 A | 1/1996 | Drummond et al. |
| 5,490,841 A | 2/1996 | Landis |
| 5,492,313 A | 2/1996 | Pan et al. |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,519,167 A | 5/1996 | Kunimoto et al. |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,516 A | 1/1998 | Peterson et al. |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| D402,538 S | 12/1998 | Wagter et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,873,540 A | 2/1999 | Hardin |
| 5,899,886 A | 5/1999 | Cosme |
| 5,911,705 A | 6/1999 | Howell |
| 5,913,846 A | 6/1999 | Szabo |
| 5,915,640 A | 6/1999 | Wagter et al. |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |

(56) References Cited

U.S. PATENT DOCUMENTS

| | | |
|---|---|---|
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| 5,992,787 A | 11/1999 | Burke |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| D456,692 S | 5/2002 | Epstein |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Bobroff et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Gilad et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,589 B1 | 6/2004 | Douglas et al. |
| 6,749,687 B1 | 6/2004 | Flaherty |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,916,017 B2 | 7/2005 | Noe |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 * | 8/2006 | Trautman et al. ............... 604/46 |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |

(56) References Cited

U.S. PATENT DOCUMENTS

| | | |
|---|---|---|
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0145073 A1 | 10/2002 | Swanson |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1* | 1/2004 | Kovelman et al. ........... 604/136 |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0064096 A1* | 4/2004 | Flaherty ............ A61M 5/14248 604/131 |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1* | 7/2004 | Funderburk et al. ......... 604/134 |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Konerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1* | 12/2005 | Bresina et al. ............ 604/93.01 |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |

(56) References Cited

U.S. PATENT DOCUMENTS

| | | |
|---|---|---|
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0247553 A2 | 9/2006 | Diermann et al. |
| 2006/0241551 A1 | 10/2006 | Lynch et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049870 A1 | 1/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Schneider et al. |
| 2007/0129691 A1 | 6/2007 | Sage, Jr. et al. |
| 2007/0173767 A1 | 7/2007 | Lynch et al. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0049865 A1 | 9/2007 | Radmer et al. |
| 2007/0185441 A1 | 9/2007 | Fangrow, Jr. |
| 2007/0213673 A1 | 9/2007 | Douglas |
| 2007/0179444 A1 | 10/2007 | Causey et al. |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 26 20 009 A1 | 12/1977 |
| DE | 28 03 509 A1 | 8/1979 |
| DE | 37 22 893 C1 | 6/1988 |
| DE | 4 342 329 A1 | 6/1994 |
| DE | 38 23 447 C3 | 2/1996 |
| DE | 196 31 921 A1 | 3/1997 |
| DE | 196 10 692 A1 | 9/1997 |
| DE | 298 18 311 U1 | 3/1999 |
| DE | 299 05 072 U1 | 9/1999 |
| DE | 19847143 A1 | 1/2000 |
| DE | 299 21 406 U1 | 11/2001 |
| DE | 100 49 001 A1 | 4/2002 |
| DE | 101 06 074 A1 | 6/2002 |
| DE | 101 17 285 A1 | 11/2002 |
| DE | 203 20 207 U1 | 11/2004 |
| EP | 0117632 B1 | 9/1984 |
| EP | 0 188 014 B1 | 10/1985 |
| EP | 0 239 244 B1 | 2/1987 |
| EP | 0272530 A2 | 6/1988 |
| EP | 0 298 521 B1 | 9/1990 |
| EP | 0451040 A1 | 10/1991 |
| EP | 0 184 231 B1 | 1/1992 |
| EP | 0 475 857 A1 | 3/1992 |
| EP | 0 544 837 B1 | 6/1993 |
| EP | 0 633 039 A1 | 7/1994 |
| EP | 0615768 A2 | 9/1994 |
| EP | 0 651 662 B1 | 5/1995 |
| EP | 0652027 A1 | 5/1995 |
| EP | 0 657 184 B1 | 6/1995 |
| EP | 0688232 B1 | 12/1995 |
| EP | 0 714 631 B1 | 6/1996 |
| EP | 744 183 A2 | 11/1996 |
| EP | 0 747 006 A1 | 12/1996 |
| EP | 0775501 B1 | 5/1997 |
| EP | 0799626 A1 | 10/1997 |
| EP | 0 688 232 B1 | 12/1998 |
| EP | 0 884 108 B1 | 12/1998 |
| EP | 0 916 361 A1 | 5/1999 |
| EP | 0 931 560 A1 | 7/1999 |
| EP | 0937475 A2 | 8/1999 |
| EP | 0 956 879 A1 | 11/1999 |
| EP | 1 045 145 A1 | 10/2000 |
| EP | 1 060 757 A1 | 12/2000 |
| EP | 1 086 718 A1 | 3/2001 |
| EP | 1 125 593 A1 | 8/2001 |
| EP | 1 167 765 A2 | 1/2002 |
| EP | 0 775 501 B1 | 6/2002 |
| EP | 0 894 216 B1 | 7/2003 |
| EP | 1329233 B1 | 7/2003 |
| EP | 1350537 A1 | 10/2003 |
| EP | 1 360 970 A1 | 11/2003 |
| EP | 1 380 315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1 475 113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 576849 | 8/1924 |
| FR | 2 611 013 A1 | 8/1988 |
| FR | 2725902 A1 | 10/1994 |
| FR | 2733915 A1 | 11/1996 |
| FR | 2 752 164 A1 | 2/1998 |
| FR | 2781617 A1 | 1/2000 |
| GB | 478803 | 1/1938 |
| GB | 591730 | 3/1946 |
| GB | 906574 | 9/1962 |
| GB | 1 268 575 | 3/1972 |
| GB | 1 403 034 | 8/1975 |
| GB | 2 088 215 A | 6/1982 |
| GB | 2 224 808 A | 5/1990 |
| GB | 2 230 702 A | 10/1990 |
| GB | 2 270 552 A | 3/1994 |
| GB | 2 423 267 A | 8/2006 |
| GB | 2 450 872 A | 7/2007 |
| GB | 2 459 101 A | 10/2009 |
| JP | A-03-191965 A | 8/1991 |
| JP | 5326062 A | 12/1993 |
| JP | 7051251 | 11/1995 |
| JP | 7051251 A | 11/1995 |
| JP | A-08-187286 A | 7/1996 |
| JP | A-10-179734 A | 7/1998 |

(56) References Cited

FOREIGN PATENT DOCUMENTS

| | | |
|---|---|---|
| JP | 2000059877 A | 2/2000 |
| JP | 3140740 B2 | 3/2001 |
| JP | 2002-028246 | 1/2002 |
| NL | 1017427 C | 11/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 87/06474 A1 | 11/1987 |
| WO | WO 9204062 A1 | 3/1992 |
| WO | WO 93/03787 A1 | 3/1993 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 95/28327 A1 | 10/1995 |
| WO | WO 96/20021 A1 | 7/1996 |
| WO | WO 96/32981 A1 | 7/1996 |
| WO | WO 96/35472 A1 | 11/1996 |
| WO | WO 98/09065 A1 | 3/1998 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 99/36009 A1 | 7/1999 |
| WO | WO 99/56802 A1 | 11/1999 |
| WO | WO 99/61815 A1 | 12/1999 |
| WO | WO 00/02614 A1 | 1/2000 |
| WO | WO 00/03757 A1 | 1/2000 |
| WO | WO 00/44324 A1 | 8/2000 |
| WO | WO 01/04507 A1 | 1/2001 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/076684 A1 | 10/2001 |
| WO | WO 01/81785 A1 | 11/2001 |
| WO | WO 01/93926 A2 | 12/2001 |
| WO | WO 02/02165 A2 | 1/2002 |
| WO | WO 02/07804 A1 | 1/2002 |
| WO | WO 02/040083 A2 | 5/2002 |
| WO | WO 02/46080 A1 | 6/2002 |
| WO | WO 02/053220 A2 | 7/2002 |
| WO | WO 02/066854 A1 | 8/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A2 | 1/2003 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2003/095003 A1 | 11/2003 |
| WO | WO 2004/012796 A1 | 2/2004 |
| WO | WO 2004/024219 A1 | 3/2004 |
| WO | WO 04/030726 A1 | 4/2004 |
| WO | WO 2004/026375 A1 | 4/2004 |
| WO | WO 2004/028457 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 04/087240 A1 | 10/2004 |
| WO | WO 2004/087240 A1 | 10/2004 |
| WO | WO 2004/098683 * | 11/2004 |
| WO | WO 2004/098683 A1 | 11/2004 |
| WO | WO 2004/101016 A1 | 11/2004 |
| WO | WO2004/101071 * | 11/2004 |
| WO | WO 2004/101071 A2 | 11/2004 |
| WO | WO 2004/110527 A1 | 12/2004 |
| WO | WO 05/004973 A1 | 1/2005 |
| WO | WO 2005/002649 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 05/046780 A1 | 5/2005 |
| WO | WO 2005/039673 A2 | 5/2005 |
| WO | WO 05/068006 A1 | 7/2005 |
| WO | WO 2005/065748 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/133702 A1 | 11/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |

(56) References Cited

FOREIGN PATENT DOCUMENTS

| | | |
|---|---|---|
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |

\* cited by examiner

INVISIBLE NEEDLE

This application claims the benefit of U.S. Provisional Application Ser. No. 60/716,222, filed Sep. 12, 2005, and EP Patent Application No. 05 019 774.8, filed Sep. 12, 2005, which are incorporated herein in their entirety.

TECHNICAL FIELD

The invention relates to an inserter for an infusion set for intermittent or continuous administration of a therapeutical substance, such as e.g. insulin. The inserter comprises a needle hub comprising an insertion needle and two spring units assuring automatic insertion and automatic retraction of the insertion needle.

BACKGROUND OF THE INVENTION

The document U.S. Pat. No. 6,387,078 pertains to an automatic injection apparatus which injects a single, pre-measured dose of stored medicine intramuscularly or transdermally, and the injection apparatus automatically retracts the hypodermic needle into the device after the injection is completed. The user presses the distal end i.e. the needle end, of the device onto the desired injection site and presses the actuation button. This releases the plunger-syringe-combination from its temporary engagement with the housing. The plunger-syringe-combination together with the spring-to-plunger-coupling are then forced away from the proximal end, i.e. the actuation end, of the housing by an energized driver spring. The driver spring propels the plunger-syringe-combination forward through the bore of the housing until the hypodermic needle exits the housing, and enters the recipient's tissue, and the syringe barrel touches the interior distal end of the housing. During this movement, a return spring positioned between the syringe assembly and the fixed, distal end of the housing becomes compressed and energized. When the liquid of the automatic injection apparatus is discharged by the plunger being pushed forward through the interior of the syringe barrel, the spring-to-plunger-coupling comes into contact with a splitter which disengages the driver spring from the plunger. Without the influence of the driver spring upon the plunger-syringe-combination, the energized return spring forces the plunger-syringe-combination to retreat rearward towards the proximal end of the device until the hypodermic needle is fully retracted into the housing.

As this automatic injection apparatus is directed toward injections of a pre-measured dose of stored liquid medicine where the plunger during injection pushes the liquid dose of stored medicine out of the apparatus, the solution will not be applicable for use when inserting an injection device as the handling and injection of a liquid under sterile conditions necessitates a complicated injection apparatus which need to interact with the liquid.

WO 2005/046780 (FIG. 97-102) describes a device used for automatic insertion of a cannula of an infusion device into the skin of a patient, and afterwards automatic retraction of the insertion needle. The insertion device has the form of an oblong cylinder (length≈4× diameter) which is open in one end (1984) and provided with means for activation at the other end (1952). When the infusion set has been loaded onto the needle (1968) the lock member (1962) is moved in direction of the end provided with means for activation by the patient using projections (1974) which projections are accessible through a slot (1976) of the housing until barbs (1956) of the lock member (1962) engage an outer surface of the housing (page 26, I. 24-27). Then the open end (1984) is placed against the skin of the patient and the means for activation (1952) is activated. When activated shoulders (1954) on the means for activation engage, the barbs (1956) are pushed toward each other in order to disengage the barbs from the housing. When the barbs are clear of the housing the lock member, the needle hub, the retainer body and the associated infusion device are moved by a first spring in direction of the open end (1984). The inserter device moves the infusion device towards the skin of the patient thereby inserting the needle and the cannula of the infusion device. As the cannula is fully inserted, barbs (1964) of the needle hub (1965) engage ramped surfaces (1972) of the sleeve (1982), causing the barbs (1964) to be forced toward one another. When the barbs (1964) have been forced sufficiently inwardly to clear ends (1988) of the main body (1980), the second spring (1966) then moves the needle hub (1965) in the direction of the activation means (1952). Thus the needle is removed from the infusion device leaving the infusion device in place on the skin while the retainer body remains in a position adjacent the open end of the sleeve so that once the insertion device is removed from the skin of the patient, the retainer body protects the patient from further contact with the needle.

This insertion device is rather complex and the length of the device is defined by the individual units forming the functional parts of the device as these units have to be placed more or less end to end. A feature illustrating the complexity of the unit is the fact that the two springs respectively biases the housing from the lock member and the retainer body from the needle hub while a main body is placed between the two spring systems to transfer the force from the first spring to the second spring.

According to the present invention the two spring units work directly together, as the first spring unit directly affects the movement of the carrier body while the second spring system is directly affected by the movement of the carrier body. That the spring units directly affect or is directly affected by the carrier body means that the spring units are connected to the carrier body directly or through a part which transfers the power either unchanged or under controlled modifications.

DESCRIPTION OF INVENTION

The object of the invention is to provide a simple, non-expensive inserter for an infusion device which inserter would be easy and safe for the user to handle during use and safe to dispose of after use.

The invention concerns an inserter for an infusion set comprising a housing, a carrier body carrying an infusion part, a needle hub, a first moving unit bringing the carrier body to a forward position and a second moving unit bringing the carrier body to a retracted position, where the inserter has means for activation which should be activated at least once in order to bring the carrier body from a retracted to a forward position, and back from the forward to the retracted position.

In a preferred embodiment the inserter has means for activation which has to be activated only once in order both to bring the carrier body from a retracted to a forward position, and back from the forward to the retracted position.

Preferably the first moving unit and the second moving unit are placed at least partly parallel to each other, where "parallel" is understood as not being "serially". "Serially" means that one moving unit is placed in extension of the other as described e.g. in WO 2005/046780. When the moving units are placed at least partly parallel they could be placed beside each other i.e. they extend over the same length or partly over the same length, or one unit could be placed inside the other if e.g. one of the units is of a kind presenting a hollow centre such as a helical spring.

In a preferred embodiment the first moving unit and the second moving unit are placed at least partly parallel to each other inside the housing. In one embodiment, the second moving unit does not extend beyond the first and second ends of the first moving unit in all positions of the needle hub.

The invention also comprises an inserter for an infusion set comprising a housing, a carrier body carrying an infusion part, a needle hub, a first spring unit and a second spring unit, where the housing is provided with guiding means on the internal surface for guiding the movement of the carrier body, the needle hub comprises an insertion needle for piercing of the skin, the carrier body has a retracted and a forward position, and in the retracted position before insertion the carrier body and the needle hub are locked to each other, the carrier body is provided with guiding means corresponding to the guiding means on the housing, the first spring unit is biasing the housing and the carrier body and the second spring unit is biasing the carrier body and the needle hub.

In a preferred embodiment the first and the second spring unit are both connected to a distal surface of the carrier body.

In another preferred embodiment the carrier body stays in a forward position after insertion of the needle.

In another preferred embodiment the infusion part is provided with an adhesive proximal surface.

In another preferred embodiment the infusion part is provided with an adhesive distal surface.

In another preferred embodiment an adhesive pad is releasably fastened to a proximal part of the housing, and the adhesive pad can cover a proximal opening of the housing through which the infusion part will be conveyed.

In another preferred embodiment the first spring unit and the second spring unit respectively comprises one compression spring.

In another preferred embodiment the carrier body is provided with at least one inclined surface which surface is in contact with a rotating part of the needle hub, which rotating part can rotate in relation to the main part of the needle hub to which the insertion needle is fastened, and the housing is provided with a member preventing the rotating part of the needle hub from rotating when the carrier body is in a retracted position.

The invention also comprises a method for inserting an infusion part where the infusion part is releasably fastened to a needle hub and the needle hub is releasably fastened to a carrier body which carrier body carries the infusion part from a retracted to a forward position, where a biased spring unit activated by the user, moves the carrier body, the needle hub and the infusion part forward from a retracted position, until a proximal surface of the infusion part contacts the patients skin or contacts a part connected to the patients skin;

at this forward position the needle hub is released from the carrier body and a biased spring unit moves the needle hub away from the carrier body resulting in the retraction of the needle hub; then the infusion part is released from the carrier body and the housing—including the carrier body and the needle hub—is removed from the patient.

DESCRIPTION OF THE DRAWINGS

The invention is explained in greater detail below with reference to the accompanying drawings wherein a preferred embodiment of the invention is shown.

In this document "distal" describes a surface or a part turned away from or placed away from the patient when the inserter is positioned with the needle end toward the patient. "Proximal" describes a surface or a part turned in direction of or placed close to the patient.

Figure 1:
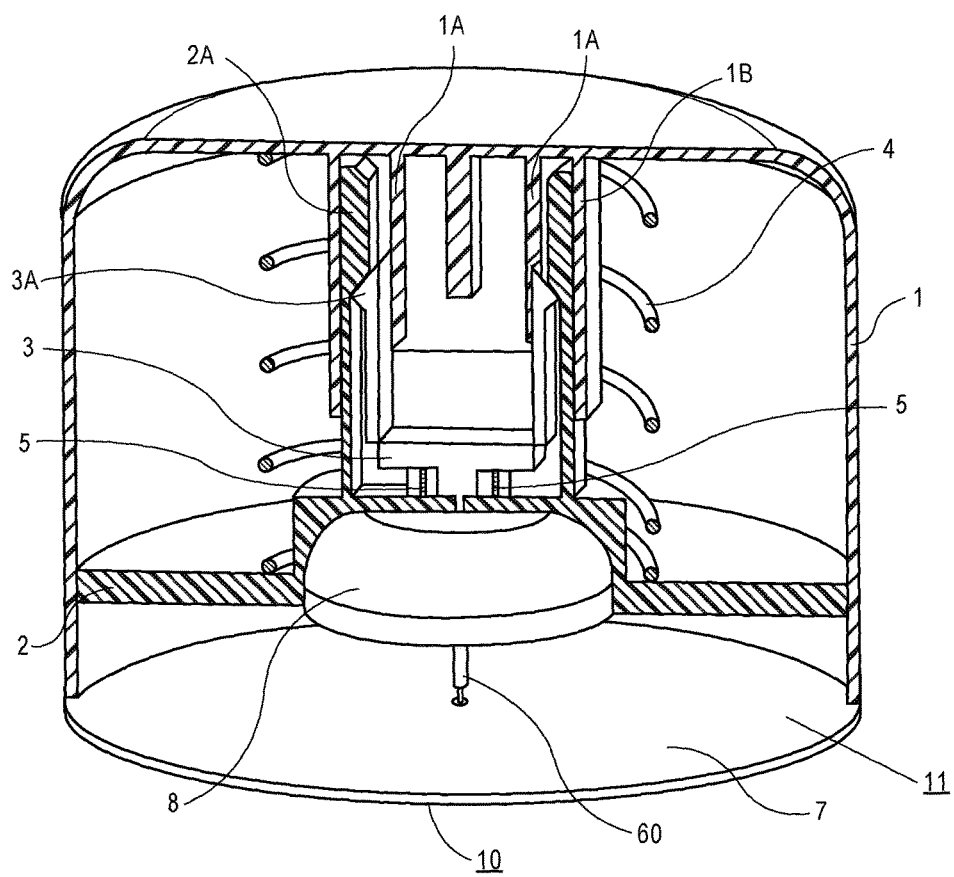
FIG. 1 is a side view of an embodiment of the inserter of the invention where the carrier body and the infusion device are in a retracted position.

The embodiment of the inserter in FIG. 1 has a housing 1 with a length a little smaller than the diameter (length≈1× diameter). The design of this inserter is mainly defined by the use and not by the constructional units inside the inserter. The constructional units of the device are few and small, and the design of the inserter such as size and shape, results from a wish of making the device easy to store and easy to handle for a user, even if the user has reduced dexterity of the hands.

The inserter comprises a carrier body 2 with at least two locking members 2a protruding from a distal surface of the carrier body. A needle hub 3 is placed between the two locking members 2a, and the needle hub is provided with members 3a protruding from a distal surface of the needle hub and corresponding to the locking means 2a of the carrier body 2. These protruding members 3a can rotate towards the center of the device along an axis through which they are also fastened to the main part of the needle hub 3. Further the needle hub is provided with an insertion needle 6 protruding from a proximal surface of the needle hub. Before insertion an infusion part 8 is fastened to the carrier body 2, the infusion part is provided with a cannula 6a which is adjoined to the insertion needle 6b in such a way that insertion of the needle 6b will result in insertion of the cannula 6a. An adhesive pad 7 with an adhesive proximal surface 10 and an adhesive distal surface 11 covers the proximal opening of the housing 1. The adhesive surface of the pad 7 will normally be covered with a release liner in order to protect the adhesive surface.

During insertion the needle hub 3 is moved from a retracted position, to a forward position and back to a retracted position by a system of springs. The system in FIG. 1-5 comprises two springs, a first spring 4 and a second spring 5. According to Hooke's law the force exerted by a spring depends on displacement of the spring x and of the spring constant k: $F_{spring}=-k\,x$. Each of the springs 4 and 5 can be replaced by more than one spring, then the spring unit replacing e.g. the first spring 4 shown in FIG. 1-5, would exert the force:

$$F_{spring} = (-k_1)\cdot x_1 + (-k_2)\cdot x_2 + \ldots + (-k_n)\cdot x_n \stackrel{as\ x_1=x_2=x_n}{=} -(k_1+k_2+\ldots+k_n)\cdot x$$

where $k_1, k_2, \ldots, k_n$ are the spring constants for the individual springs, and $F_{spring}=-k\cdot x$, where $k=k_1+k_2+\ldots+k_n$.

The first spring 4 and the second spring 5 can comprise both compression and tension springs.

In the embodiment of FIG. 1-5, the housing 1 is provided with guiding means 1a and 1b. The guiding means 1a and 1b comprises parallel walls, an inner wall 1a and an outer wall 1b, protruding from the distal inner surface of the housing 1. The locking members 2a of the carrier body 2 and the protruding members 3a of the needle hub 3 are placed between the parallel walls 1a and 1b. The locking members 2a have one or more inclined surfaces which are in contact with a part of the protruding members 3a. When the carrier body 2 is pulled or pushed towards the patient's skin, the locking members 2a will exert a force on and perpendicular to each inclined surface. This force has one component parallel to the walls 1a and 1b pointing in same direction as the movement, and another component perpendicular to the first component pointing toward the inner wall 1a. As long as the inner wall 1a is present, a force of same size but opposite direction as the second component will push back from the inner wall 1a keeping the protruding member 3a in a steady position between the walls 1a and 1b. When the inner wall 1a is not present the second component of the force exerted by the locking member will push the protruding members 3a towards the center of the device.

When the protruding members 3 have been released from interlocking with the locking members 2a, the needle hub is not influenced by a force in direction of the infusion part, and the force exerted by the second string 5 will overcome the friction between the insertion needle and the cannula extending from the infusion part 8 and move the needle hub 3 away from the infusion part 8.

In FIG. 1 the carrier body 2 is placed and locked in a retraced position. The insertion needle 6 which is adjoined to the cannula is seen below the infusion part 8. Both the spring units 4 and 5 are biased, and the locking members 2a is interlocked with the protruding members 3a of the needle hub 3 due to support of the inner walls 1a.

When the user wants to insert the infusion device, the device is first placed on the insertion site on the patient. Then the inserter is activated by the user by unlocking the carrier body 2 from the housing 1.

It is not shown on this embodiment how unlocking of the carrier body 2 is done but one way is to provide the carrier body 2 with two members protruding into openings of the housing 1 opposite each other. Unlocking of the carrier body is then performed by the user pressing on the housing 1 at two opposite points placed on a line perpendicular to the line formed by the two protruding members of the carrier body 2. Pressing on the two points on the perpendicular line will cause a deformation of the housing 1 and increase the distance between the two corresponding openings in the housing 1, the protruding members of the carrier body will then be released from the housing 1.

Figure 2:
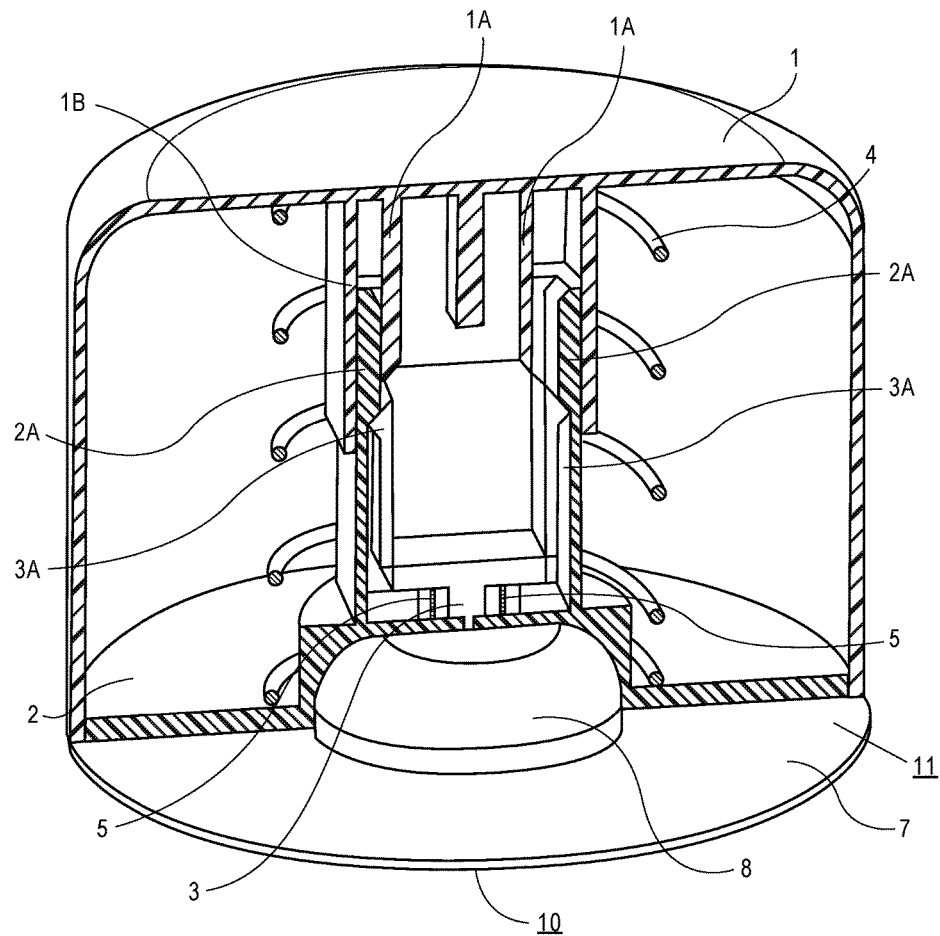
FIG. 2 is a side view of the inserter with the carrier body and the infusion device in an advanced position where the needle hub is locked to the carrier body.
Figure 3:
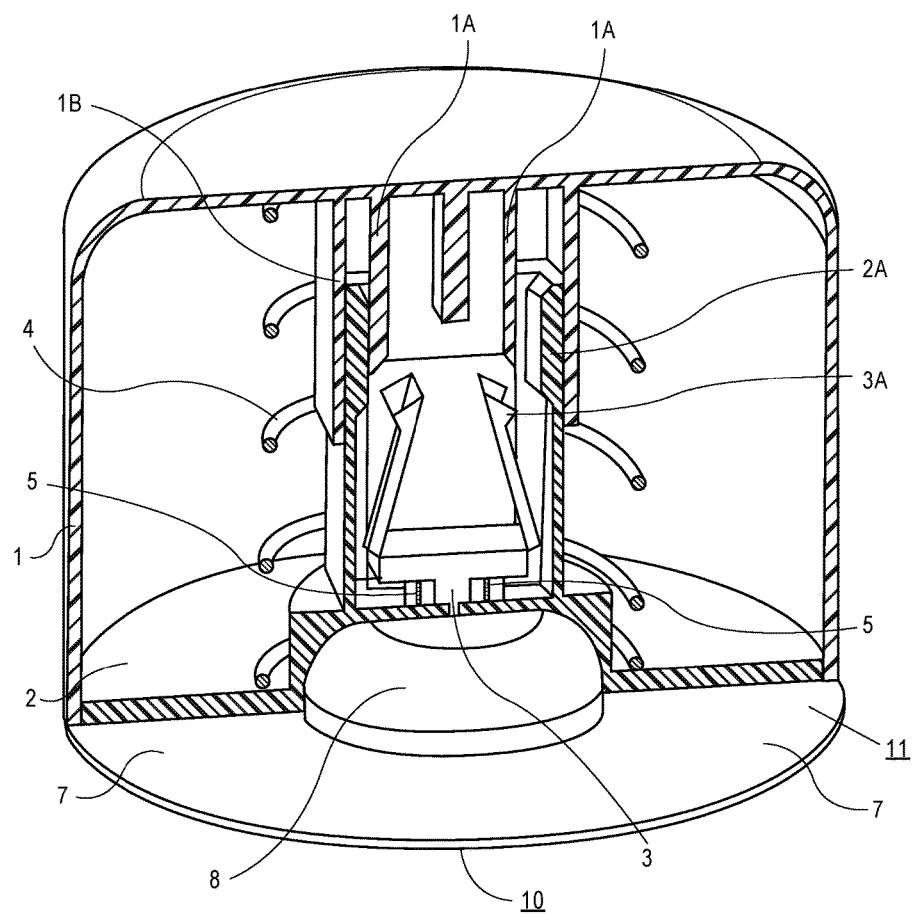
FIG. 3 is a side view of the inserter with the carrier body and the infusion device in an advanced position where the needle hub has been released from the carrier body.

When the inserter is activated the first string 4 tries to return to an unbiased position and doing this brings the carrier body 2 and the infusion part 8 to a forward position shown in FIG. 2.

In this forward position the insertion needle 6 and the adjoined cannula have penetrated the adhesive pad 7 placed at the proximal end of the housing 1. The protruding members 3a of the needle hub 3 have in FIG. 2 been released from the support of the inner walls 1a, and as soon as the release from the inner walls 1a has taken place the protruding members 3a of the needle hub will be forced towards the center of the inserter to the position shown in FIG. 3.

Figure 4:
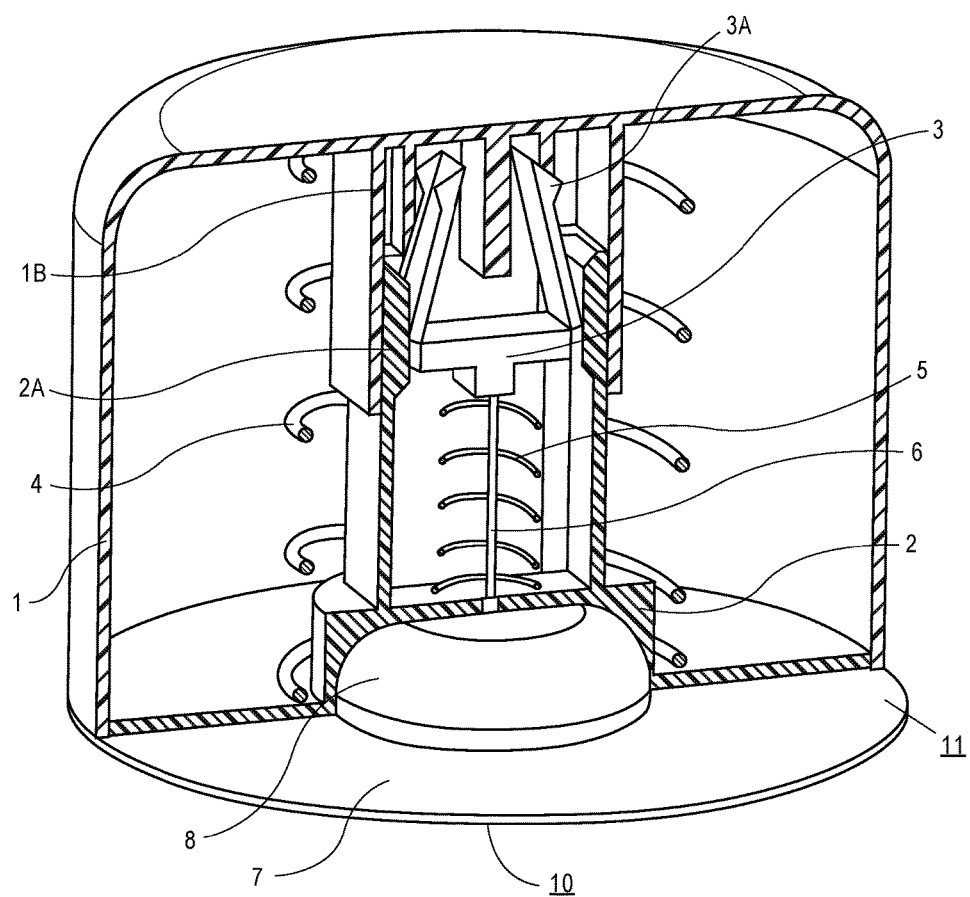
FIG. 4 is a side view of the inserter with the carrier body and the infusion device in an advanced position where the needle hub is in a retracted position.

Immediately after the protruding members 3a of the needle hub are free of the inner walls 1a, the upward force from the spring unit 5 will bring the needle hub 3 to the position shown in FIG. 4, where the needle hub 6 and the insertion needle 6 is fully covered by the housing 1.

Figure 5:
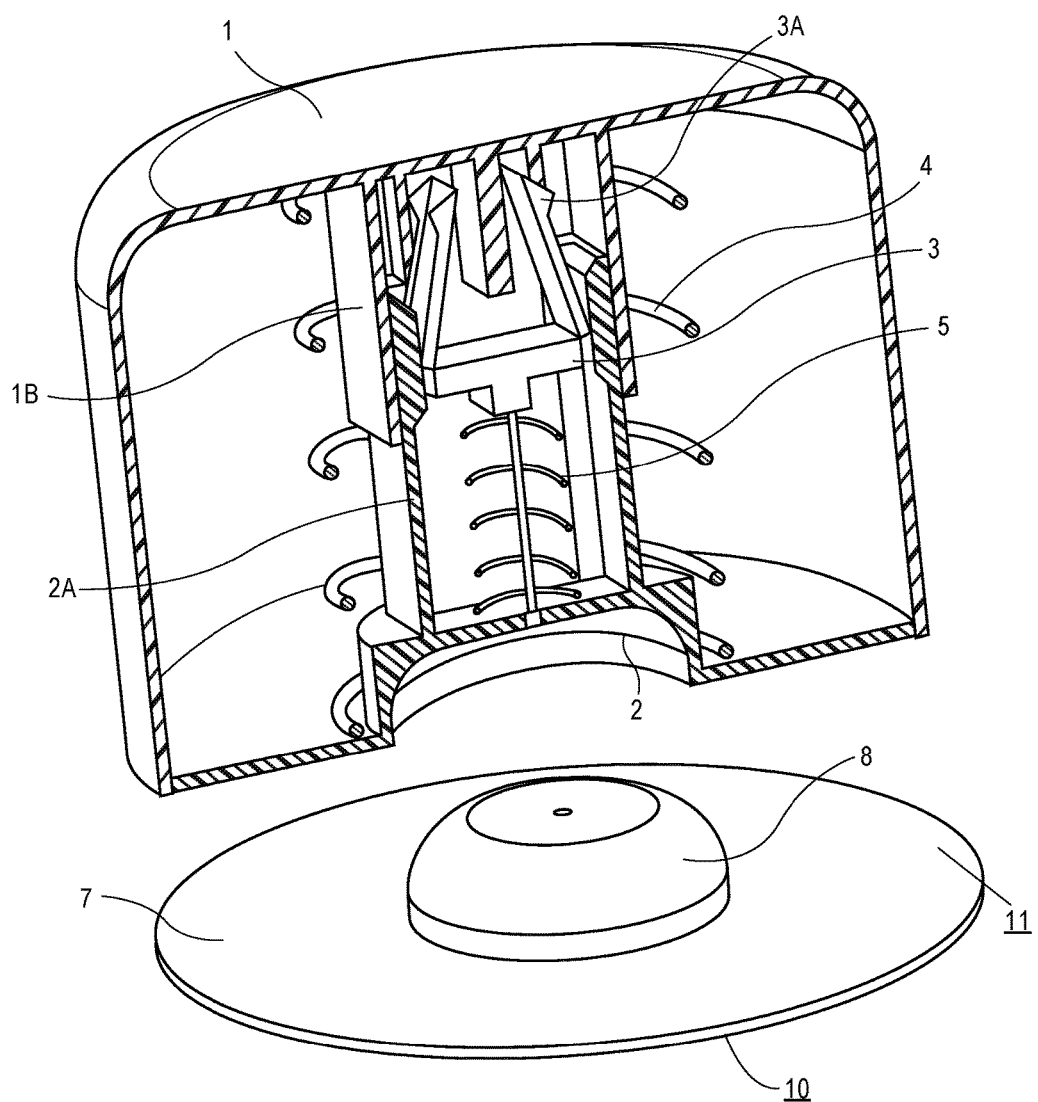
FIG. 5 is a side view of the inserter after the inserter has been removed from the patient leaving the infusion part on the patient's skin.

In FIG. 5 it is shown how the infusion part 8 has been secured to the adhesive pad 7, the pad 7 is secured to the patient, and then the inserter is removed and can be disposed of in a safe way together as the contaminated insertion needle 6 is placed behind the protective walls of the inserter housing 1.

The invention claimed is:

1. An inserter for an infusion set comprising
   a housing;
   a carrier body carrying an infusion part, the infusion part adjoined to a cannula and configured to be releasable from the carrier body;
   an insertion needle, the insertion needle secured to a needle hub;
   the carrier body moveable between a retracted position and a forward position;
   wherein when the carrier body is in the forward position, the infusion part is configured to contact a patient's skin or an adhesive pad on the patient's skin; and
   wherein when the carrier body is in the retracted position, the infusion part is configured to be away from the patient's skin;
   a first moving unit biasing the carrier body to the forward position when the carrier body is in the retracted position; and
   a second moving unit biasing the needle hub away from the carrier body when the carrier body is in the forward position;
   wherein after insertion of the insertion needle and the cannula, the second moving unit is configured to retract the insertion needle from the patient's skin and at least a portion of the insertion needle is positioned inside the housing, and wherein the first moving unit and the second moving unit are placed at least partly parallel to each other and the second moving unit does not extend beyond first and second ends of the first moving unit in all positions of the needle hub.

2. The inserter of claim 1, wherein the first and the second moving units both are connected to a distal surface of the carrier body.

3. The inserter of claim 1, wherein the first moving unit and the second moving unit are placed inside the housing, and the housing comprises a proximal end with a proximal opening.

4. The inserter of claim 1, wherein
   the housing comprises an internal surface and a guiding means is provided on the internal surface for guiding a movement of the carrier body,
   the carrier body is provided with locking members corresponding to the guiding means of the housing,
   and in the retracted position of the carrier body, the carrier body and the needle hub are locked to each other.

5. The inserter of claim 4, wherein the adhesive pad is placed at a proximal end of the housing.

6. The inserter of claim 5, wherein the adhesive pad covers a proximal opening of the housing through which the infusion part is conveyed.

7. The inserter of claim 5, wherein the first moving unit and the second moving unit each comprise a compression spring.

8. The inserter of claim 4, wherein the carrier body is provided with at least one inclined surface, wherein the at least one inclined surface is in contact with a protruding member of the needle hub, which protruding member can rotate in relation to the needle hub, and the housing is provided with locking members preventing the protruding member of the needle hub from rotating when the carrier body is in the retracted position.

9. The inserter of claim 1, wherein the carrier body stays in the forward position after insertion of the needle.

10. The inserter of claim 1, wherein the adhesive pad comprises an adhesive proximal surface.

11. The inserter of claim 1, wherein the adhesive pad comprises an adhesive distal surface.

12. The inserter of claim 1, wherein the insertion needle extends at least partially through the infusion part before insertion of the infusion part.

13. The inserter of claim 1, wherein the carrier body stays in the forward position after the infusion part is configured to contact the patient's skin and the insertion needle is configured to be retracted from the patient's skin.

14. The inserter of claim 1, wherein the needle hub extends distal to the carrier body within the housing.

15. The inserter of claim 1, wherein the needle hub comprises at least one protruding member releasably lockable with the carrier body.

16. The inserter of claim 15, wherein the at least one protruding member releasably locks with at least one locking member of the carrier body.

17. The inserter of claim 16, wherein the at least one protruding member and the at least one locking member are positioned between parallel walls of the housing.

18. The inserter of claim 1, wherein the first moving unit and the second moving unit each comprise a compression spring.

19. The inserter of claim 1, wherein the first moving unit is located between the carrier body and the housing, and the second moving unit is located between the carrier body and the needle hub.

20. An inserter for an infusion set comprising
a housing,
a carrier body comprising at least one inclined surface, the carrier body carrying an infusion part, the infusion part adjoined to a cannula and configured to be releasable from the carrier body,
an insertion needle, the insertion needle secured to a needle hub; the needle hub comprising at least one protruding member;
wherein the carrier body has a forward position and a retracted position,
wherein in the carrier body's retracted position, the infusion part is configured to be away from a patient's skin and the needle hub's at least one protruding member is configured to maintain contact with the carrier body's at least one inclined surface,
wherein in the carrier body's forward position, the infusion part is configured to contact the patient's skin an adhesive on the patient's skin and the needle hub's at least one protruding member is configured to release contact with the carrier body's at least one inclined surface;
a first moving unit biasing the carrier body to the forward position when the carrier body is in the retracted position; and
a second moving unit positioned between the carrier body and at least part of the needle hub, the second moving unit biasing the needle hub away from the carrier body when the carrier body is in the forward position, wherein after insertion of the insertion needle and the cannula, the insertion needle is configured to retract from the patient's skin and at least a portion of the insertion needle is positioned inside the housing, and wherein the first moving unit and the second moving unit are at least partly parallel to each other and the second moving unit does not extend beyond first and second ends of the first moving unit in all positions of the needle hub.

21. The inserter set of claim 20, wherein the housing comprises an inner member for maintaining contact between the needle hub's at least one protruding member and the carrier body's at least one inclined surface when the carrier body is in the retracted position.

22. The inserter of claim 20, wherein the first moving unit is located between the carrier body and the housing, and the second moving unit is located between the carrier body and the needle hub.

23. An inserter for an infusion set comprising
a housing comprising an internal surface;
a carrier body connected to an infusion part, the infusion part adjoined to a cannula and configured to be releasable from the carrier body;
an insertion needle secured to a needle hub;
wherein the carrier body has a forward position and a retracted position;
wherein the infusion part is configured to contact a patient's skin or an adhesive on the patient's skin in the forward position, and is configured to be away from the patient's skin in the retracted position;
a first moving unit between the carrier body and the housing, the first moving unit biasing the carrier body to the forward position when the carrier body is in the retracted position; and
a second moving unit between the carrier body and at least part of the needle hub when the carrier body is in the retracted position, the second moving unit configured to bias the needle hub and the insertion needle away from the patient's skin after insertion of the insertion needle and the cannula,
wherein the housing's internal surface is located at least partly within the first moving unit and configured to maintain the carrier body in the retracted position,
wherein after insertion of the insertion needle and the cannula, the second moving unit is configured to retract the insertion needle from the patient's skin and at least a portion of the insertion needle is positioned inside the housing, and wherein the first moving unit and the second moving unit are placed at least partly parallel to each other and the second moving unit does not extend beyond first and second ends of the first moving unit in all positions of the needle hub.

24. An inserter for an infusion set comprising:
a housing comprising an internal member,
a needle hub comprising at least one rotating member,
a carrier body comprising at least one protruding member, the carrier body carrying an infusion part, the infusion part releasably connected to the needle hub, the needle hub releasably connected to the carrier body, two biased spring units;

means for activating the two biased spring units, wherein when activated, a first of the two biased spring units is capable of moving the carrier body, needle hub and infusion part from a retracted position to a forward position until a proximal surface of the infusion part contacts a patient's skin or an adhesive on the patient's skin, and a second of the two biased spring units is capable of moving the needle hub from a forward position to a retracted position away from the carrier body, wherein when the carrier body is in the retracted position, the housing's internal member is configured to maintain the needle hub's at least one rotating member in contact with the carrier body's at least one protruding member, and wherein when the carrier body is in the forward position, the housing's internal member is configured to release the needle hub's at least one rotating member from contact with the carrier body's at least one protruding member such that the needle hub's at least one rotating member rotates about the needle hub.

25. The inserter of claim 24, wherein the at least one rotating member rotates inward about the needle hub.

* * * * *